(12) United States Patent
Morrical et al.

(10) Patent No.: US 7,544,469 B2
(45) Date of Patent: Jun. 9, 2009

(54) METHODS AND COMPOSITIONS FOR OPTICAL DETECTION OF SINGLE-STRANDED POLYNUCLEOTIDES

(75) Inventors: Scott Morrical, South Burlington, VT (US); Na Qian, Colchester, VT (US)

(73) Assignee: The University of Vermont and State Agricultural College, Burlington, VT (US)

( * ) Notice: Subject to any disclaimer, the term of this patent is extended or adjusted under 35 U.S.C. 154(b) by 412 days.

(21) Appl. No.: 10/542,336

(22) PCT Filed: Jan. 12, 2004 (Under 37 CFR 1.47)

(86) PCT No.: PCT/US2004/000665

§ 371 (c)(1), (2), (4) Date: Oct. 25, 2006

(87) PCT Pub. No.: WO2004/063352

PCT Pub. Date: Jul. 29, 2004

(65) Prior Publication Data

US 2007/0178455 A1    Aug. 2, 2007
US 2009/0011404 A9    Jan. 8, 2009

Related U.S. Application Data

(60) Provisional application No. 60/440,059, filed on Jan. 13, 2003.

(51) Int. Cl.
    *C07K 14/00* (2006.01)
(52) U.S. Cl. .......................................... 435/6; 530/350
(58) Field of Classification Search ........................ None
See application file for complete search history.

(56) References Cited

OTHER PUBLICATIONS

Villemain et al. 1993; Energetics of arginine-4 substitution mutants in the N-terminal cooperativity domain of T4 gene 32 protein. Biochemistry 32: 11235-11246.*
Xu et al. 2001; Helicase assembly protein Gp59 of bacteriophage T4: Fluorescence anisotropy and sedimentation studies of complexes formed with derivatives of Gp32, the phage ssDNA binding protein. Biochemistry 40: 7651-7661.*
en.wikipedia.org/wiki/Fluorescent_labelling; Dec. 12, 2008.*
Chase, J.W. et al. Single-stranded DNA binding proteins required for DNA replication. Annu Rev Biochem. 55: 103-136, 1986.
Harris, L.D. et al. Formation of D loops by the UvsX protein of T4 bacteriophage: a comparison of the reaction catalyzed in the presence of absence of gene 32 protein. Biochemistry. 27(18): 6954-6959, 1988.
Huang, H. et al. Fidelity and predominant mutations produced by deep vent wild-type and exonuclease-deficient DNA polymerases during in vitro DNA amplification. DNA Cell Biol. 15(7): 589-594, 1996.
Kelly et al. DNA "melting" proteins III: Flourescence "mapping" of the nucleic acid binding site of bacteriophage T4 gene 32-protein. Journal of Biological Chemistry 251(22): 7229-7239, 1976.
Kelly et al. DNA "melting" proteins IV: Flourescence measurements of binding parameters for bacteriophage T4 gene 32-protein to mono-, oilgo-, and polynucleotides. Journal of Biological Chemistry 251(22): 7240-7250, 1976.
Kowalczykowski, S.C. et al. Cooperative and noncooperative binding of protein ligands to nucleic acid lattices: experimental approaches to the determination of thermodynamic parameters. Biochemistry. 25(6): 1226-1240, 1986.
Kroutil, L.C. et al. Effect of accessory proteins on T4 DNA polymerase replication fidelity. J Mol Biol. 278(1): 135-146, 1998.
Muniyappa, K. et al. Mechanism of the concerted action of recA protein and helix-destabilizing proteins in homologous recombination. Proc Natl Acad Sci U S A. 81(9): 2757-2761, 1984.
Shamoo, Y., et al. Crystal structure of a replication fork single-stranded DNA binding protein (T4 gp32) complexed to DNA. Nature. 376(6538): 362-366, 1995.
Villemain, J.L. et al. Mutations in the N-terminal cooperativity domain of gene 32 protein alter properties of the T4 DNA replication and recombination systems, J Biol Chem. 275(40): 31496-31504, 2000.
Yonesaki, T. et al. Synergistic action of three recombination gene products of bacteriophage T4, uvsX, uvsY, and gene 32 proteins. J Biol Chem. 264(14): 7814-7820, 1989.

* cited by examiner

*Primary Examiner*—Karen Cochrane Carlson
(74) *Attorney, Agent, or Firm*—Wolf, Greenfield & Sacks, P.C.

(57) ABSTRACT

New Gp32F protein for determining, localizing or quantitating single-stranded DNA or RNA molecules comprises a Gp32 protein conjugated at an environment-sensitive amino acid (e.g. cysteine-166) to a fluorescent label.

17 Claims, 8 Drawing Sheets

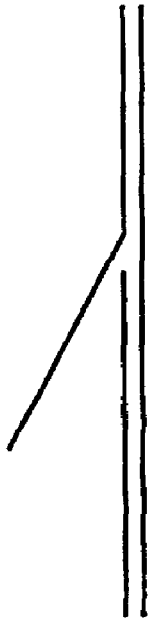
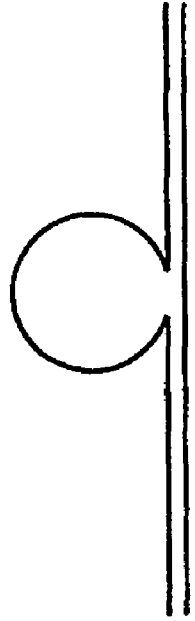
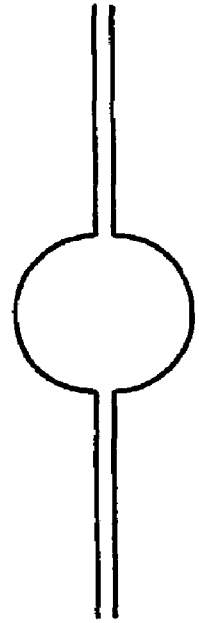

Fig. 4

QUANTITATIVE FLUOROMETRIC MEASUREMENTS OF DNA AND RNA TRANSACTIONS USING Gp32F

| REACTION | SUBSTRATE | | | SIGNNAL CHANGE |
|---|---|---|---|---|
| A. EXONUCLEASE | ssDNA or ssRNA | → | \| | DECREASE |
| | ds POLYNUCLEOTIDE | → | ‖ | INCREASE |
| B. HELICASE | ds POLYNUCLEOTIDE | → | Y | INCREASE |
| C. REANNEALING, HYBRIDIZATION | COMPLEMENTARY ss POLYNUCLEOTIDES | → | ‖ | DECREASE |
| D. REPLICATION, REVERSE TRANSCRIPTION | PRIMED ss TEMPLATE | → | ‖ | DECREASE |
| | NICKED ds TEMPLATE | → | ‖/ | INCREASE |
| E. DNA REPAIR/GAP FORMATION | NICKED ds POLYNUCLEOTIDES | → | = | INCREASE |
| F. HOMOLOGOUS RECOMBINATION: (i) PRESYNAPSIS | ssDNA | ∘RECOMBINASE + ═══ → | ▭▭▭ FILAMENT | DECREASE |
| (ii) DNA STRAND EXCHANGE | HOMOLOGOUS ssDNA & dsDNA | ▭▭▭ + ═══ → | ▭▭▭ + ═══ | INCREASE |

US 7,544,469 B2

METHODS AND COMPOSITIONS FOR OPTICAL DETECTION OF SINGLE-STRANDED POLYNUCLEOTIDES

RELATED APPLICATIONS

This application is the national stage application of PCT/US04/00665, filed Jan. 12, 2004 and claims priority under 35 U.S.C. §119 to U.S. 60/440,059, filed Jan. 13, 2003, the entire contents of which is hereby incorporated by reference.

GOVERNMENT SUPPORT

This invention was made with government support awarded by the National Institutes of Health under Grant Number GM48847. The Government has certain rights in the invention.

FIELD OF THE INVENTION

The invention relates to methods and products for optical detection of single-stranded polynucleotides. The invention is useful for detection and/or visualization of single-stranded DNA or RNA molecules.

BACKGROUND OF THE INVENTION

Gp32 is the single-stranded DNA (ssDNA)-binding protein of bacteriophage T4, which binds specifically, stoichiometrically, and with high affinity and cooperativity to single-stranded polynucleotides (Chase, J. W., et al. (1986) *Annu Rev Biochem.* 55, 103-36.). Gp32 plays a role in T4 DNA replication and recombination processes, by coating and stabilizing ssDNA regions generated. during DNA synthesis and recombination transactions. Gp32 binding removes secondary structure from ssDNA. Gp32 also binds to single-stranded RNA (ssRNA) molecules and thereby autoregulates its own translation. Gp32 has little or no affinity for double-stranded DNA or RNA molecules. In addition to ssDNA/ssRNA binding activities, biochemical activities ascribed to Gp32 include but are not limited to (Chase, J. W., et al. (1986) *Annu Rev Biochem.* 55, 103-36; Harris, L. D., et al. (1988) *Biochemistry.* 27(18), 6954-9; Kroutil, L. C., et al. (1998) *J Mol Biol.* 278(1), 135-46; Muniyappa, K., et al. (1984) *Proc Natl Acad Sci USA.* 81(9), 2757-61; Yonesaki, T., et al. (1989) *J Biol Chem.* 264(14), 7814-20.): (a) stimulation of T4 gp43 DNA polymerase; (b) stimulation of DNA strand exchange reactions promoted by T4 recombination proteins UvsX/UvsY and by *E. coli* recombination protein RecA; and (c) promoting reannealing between complementary ssDNA molecules. Gp32 is used in concert with T4 gp43 and other commercially available DNA polymerases and reverse transcriptases during various molecular biology protocols. Specifically, Gp32 is used to eliminate polymerase pausing at sequences of strong ssDNA secondary structure during DNA sequencing and site-directed mutagenesis procedures (Kroutil, L. C., et al. (1998) *J Mol Biol.* 278(1), 135-46.). Gp32 is also used to increase the fidelity and length of polymerase chain reaction (PCR) products generated by Taq and other thermostable DNA polymerases (Huang, H., et al. (1996) *DNA Cell Biol.* 15(7), 589-94.). Gp32 can also be used in electron microscopy as a cytological marker for ssDNA (Harris, L. D., et al. (1988) *Biochemistry.* 27(18), 6954-9.).

SUMMARY OF THE INVENTION

The invention relates in part to the use of Gp32 protein for the detection of polynucleotides. We have conjugated labels to Gp32 and mutant Gp32 molecules that are useful for the detection of polynucleotides. The invention includes the use of the Gp32 proteins and mutant Gp32 proteins to identify strandedness of polynucleotides including changes between single-strand polynucleotides and double-strand polynucleotides. The compounds and methods we have identified are in part useful in assays, diagnostics, and reactions for the detection of polynucleotide molecules.

According to one aspect of the invention, a Gp32F protein is provided. The GP32F protein includes a Gp32 protein conjugated at an environment-sensitive amino acid to a fluorescent label that fluoresces at a first intensity when the Gp32 protein is not bound to a single-stranded polynucleotide and fluoresces at a second intensity when the Gp32 protein is bound to a single-stranded polynucleotide. In some embodiments, the Gp32 protein is a mutant Gp32 protein. Preferably the environment-sensitive amino acid is selected from the group consisting of cysteine-166, Serine-195 mutated to cysteine, Lysine-51 and Lysine-207. Most preferably, the environment-sensitive amino acid is cysteine-166.

In certain embodiments, the mutant Gp32 protein is selected from the group consisting of Gp32-A, R4K, Gp32, K3A, R4Q, R4T, R4G, Gp32-B, and CORE. In other embodiments, the mutant Gp32 protein is a truncated Gp32 protein. In still other embodiments, the mutant Gp32 protein is a Gp32 protein in which the cysteine at position 166 has been moved to another amino acid position in the Gp32.

The fluorescent label can be selected from labels known to one of ordinary skill in the art, including fluorescein, BODIPY, Alexa Fluor, Oregon Green, tetramethylrhodamine, Rhodamine Red, Texas Red, pyridyloxazole,; benzoxadiazole derivatives including NBD halides and iodoacetamides, SBD; Lucifer Yellow, iodoacetamide; stilbene, coumarin,; napthalene, aziridine, dapoxyl, pyrene, and bimanes.

In some embodiments, the single-stranded polynucleotide is tethered to a surface. In these embodiments, the surface preferably is selected from the group consisting of: a bead, a slide, a microtiter plate, a membrane, and a filter.

According to another aspect of the invention, methods of detecting single-stranded polynucleotides in a sample are provided. The methods include (a) contacting a sample with a Gp32F protein and (b) detecting fluorescence of the Gp32F protein bound to the sample as an indication of single-strand polynucleotides in the sample. In some embodiments, the methods further include a step of separating bound Gp32F protein from unbound Gp32F protein.

Preferably, the fluorescence is detected with a method selected from the group consisting of visualization, spectrophotometry, microscopy, video microscopy, digital microscopy, digital imaging, and fluorescence plate reader methods. In some embodiments, the sample is selected from the group consisting of: a solution, a reaction mixture, and an electrophoretic gel. In other embodiments, the sample is attached to a surface. Preferably, the surface is selected from the group consisting of a filter, a membrane, a glass slide, a tube, a bead, and a microtiter plate.

In still other embodiments, the Gp32F protein is a mutant Gp32F protein.

In further embodiments, the sample comprises a tissue, cell, or fragment thereof. Preferably these methods also include determining the localization of the single-stranded polynucleotides in the cell, tissue, or fragment thereof.

In certain embodiments, the single-stranded polynucleotide is selected from the group consisting of single-stranded DNA and single-stranded RNA. Preferably, the single-stranded polynucleotide is a gap, tail, flap, loop, or bubble in a double-stranded polynucleotide. In other embodiments, the single-stranded polynucleotide is an unpaired heterologous polynucleotide in a hybridization product selected from the group consisting of: DNA-DNA, RNA-DNA, and RNA-RNA hybridization products.

According to still another aspect of the invention, methods of determining the quantity of single-stranded polynucleotide in a sample, including (a) contacting a sample with a Gp32F protein and (b) determining the intensity of fluorescence in the sample, wherein the intensity of fluorescence indicates the quantity of single-stranded polynucleotide in the sample.

In some embodiments, the methods also include a step of separating Gp32F protein bound to single-stranded polynucleotides in the sample to from unbound Gp32F protein.

In other embodiments, the methods include comparing the intensity detected in step (b) with a control intensity as an indication of the quantity of single-stranded polynucleotide in the sample. Preferably the control intensity is the level of fluorescence in the Gp32F protein not contacted with the sample or a standard curve of fluorescence intensity. The intensity of fluorescence can be detected with a method selected from the group consisting of visualization, spectrophotometry, microscopy, video microscopy, digital microscopy, digital imaging, and fluorescence plate reader methods.

In other embodiments, the sample is selected from the group consisting of: a solution, a reaction mixture, and an electrophoretic gel. In certain of these embodiments, the sample is attached to a surface, preferably one selected from the group consisting of a filter, a membrane, a glass slide, a tube, a bead, and a microtiter plate.

In still other embodiments, the reaction mixture comprises a reaction selected from the group consisting of: exonucleolytic degradation of DNA or RNA; helicase-catalyzed unwinding of double-stranded DNA, RNA, or RNA-DNA; reannealing of complementary single-stranded polynucleotides to form duplex; DNA replication; DNA reverse transcription, formation of excision gaps during DNA mismatch repair; nucleotide excision repair reactions; homologous genetic recombination-DNA strand exchange reactions; and presnaptic filament formation.

The reaction mixture for these methods can include a tethered polynucleotide.

In further embodiments, the sample comprises a tissue, cell, or fragment thereof, and the methods thus can include determining the localization of the single-stranded polynucleotides in the cell, tissue, or fragment thereof.

Preferably, the single-stranded polynucleotide is selected from the group consisting of single-stranded DNA and single-stranded RNA, or is a gap, tail, flap, loop, or bubble in a double-stranded polynucleotide, or is an unpaired heterologous polynucleotide in a hybridization product selected from the group consisting of: DNA-DNA, RNA-DNA, and RNA-RNA hybridization products.

In certain embodiments, the Gp32F protein is a mutant Gp32F protein. In other embodiments, the step of determining the level of fluorescence is repeated one or more times. The step of determining the level of fluorescence can be done in real-time, wherein a change in the level of fluorescence over time indicates a change in the quantity of single-stranded polynucleotide in the sample over time. The step of determining the level of fluorescence also can be done using time-resolved imaging or photon counting.

According to another aspect of the invention, methods of making a Gp32F protein are provided, including modifying a Gp32 protein, and conjugating the modified Gp32 protein to a fluorescent label. Preferably the method also include contacting the fluorescently labeled Gp32 protein with a single-stranded polynucleotide, and determining whether or not there is increased fluorescence intensity compared to a control not contacted with a single-stranded polynucleotide.

In some embodiments, modifying is a making a modification selected from the group consisting of: truncation, deletion, addition, and substitution, or is altering the position of cysteine-166 in the amino acid sequence of Gp32 protein.

The fluorescein preferably is conjugated to the Gp32 protein at the cysteine-166 position.

According to another aspect of the invention, kits are provided. The kits include a first container containing Gp32F protein, and instructions for the use of the Gp32F to detect single-stranded polynucleotides. Preferably, the kits also include a container containing an intercalating dye and instructions for using the dye to detect double-stranded polynucleotides, and/or a container containing a fluorescent label that fluoresces at a wavelength different from the fluorescein in the first container, and instructions for using the fluorescent label in double labeling or fluorescent resonance energy transfer (FRET) reactions.

According to yet another aspect of the invention, kits are provided. The kits include a first container containing Gp32 protein, a second container containing a fluorescein label, and instructions for conjugating the Gp32 protein to the fluorescein label to make Gp32F protein, and instructions for using the Gp32F protein to detect single-stranded polynucleotides. Preferably, the kits also include a container containing an intercalating dye and instructions for using the dye to detect double-stranded polynucleotides, and/or a container containing a fluorescent label that fluoresces at a wavelength different from the fluorescein in the first container, and instructions for using the fluorescent label in double labeling or fluorescent resonance energy transfer (FRET) reactions.

According to yet another aspect of the invention, methods of evaluating Gp32F functional activity in a candidate Gp32F protein are provided. The methods include (a) contacting a sample containing a single-stranded polynucleotide with a candidate Gp32F protein, (b) determining the fluorescence of the candidate Gp32F protein, and (c) comparing the fluorescence of the candidate Gp32F protein to a control, wherein a higher fluorescence intensity in (b) than the fluorescence intensity of the control indicates that the candidate Gp32F has Gp32F functional activity.

In some embodiments, the control intensity is the intensity of the fluorescence of the candidate Gp32F protein that is not contacted with a single-stranded polynucleotide, or the control intensity is the intensity of the fluorescence of the single-stranded polynucleotide not contacted with a Gp32F protein. In other embodiments, the Gp32F protein functional activity is binding to single-stranded polynucleotides. Preferably, the Gp32F protein functional activity is the increase in fluorescence intensity of the Gp32F protein upon binding to a single-stranded polynucleotide.

BRIEF DESCRIPTION OF THE DRAWINGS

FIG. 3 shows diagrams of polynucleotide structures recognized by Gp32F.

FIG. 4 shows polynucleotide transactions (indicated as FIG. 4A through FIG. 4F), for which quantitative fluorometric measurements of DNA and RNA can be done using Gp32F. The far right column indicates the direction of the fluorescence intensity change with the progression of each of the reaction types.

FIG. 7 shows two graphs demonstrating changes in extrinsic fluorescence of fluorescein-Gp32 that report on Gp32-ssDNA association/dissociation.

DETAILED DESCRIPTION OF THE INVENTION

We have discovered that protein conjugates that include the bacteriophage T4 gene 32 protein (Gp32) can be covalently linked to a detectable label, for example a fluorescent molecule, and are useful as markers for polynucleotides. We have discovered that labeled Gp32 can be used as a marker for polynucleotides, including, but not limited to single-stranded polynucleotides. In addition, we have discovered that a protein conjugate consisting of the bacteriophage T4 gene 32 protein (Gp32) covalently linked to a fluorescent molecule at amino acid residue cysteine-166 exhibits a shift in fluorescence intensity when Gp32F protein binds to single-stranded polynucleotides. This surprising feature allows Gp32F protein to be utilized in methods to detect and monitor structures and reactions that include single-stranded polynucleotides. This composition is useful in methods including, but not limited to methods involving detection, imaging, and/or quantification of single-stranded polynucleotides via the fluorescence signature of the fluorescent moiety of a Gp32F protein.

In some aspects the invention includes conjugation of a fluorescent molecule (e.g. fluorescein) to the cysteine in the 166 position of wild-type and mutant Gp32 protein. These molecules, termed Gp32F and mutant Gp32F, specifically bind to single-stranded polynucleotides and are useful for their detection in solutions, reactions and other samples. Gp32F protein and mutant Gp32F proteins are useful for specific fluorescent detection of single-stranded polynucleotides, even against a high background of double-stranded polynucleotides. We have discovered that the fluorescence of Gp32F protein and mutant Gp32F protein changes upon polynucleotide binding (see FIG. 1), which makes possible an array of novel assays for nucleic acids transactions as described herein (see Examples section). The occurrence of single-stranded regions in a variety of nucleic acids and intermediates allows the use of the Gp32F proteins in many areas of biomedical research and clinical applications.

Figure 2:
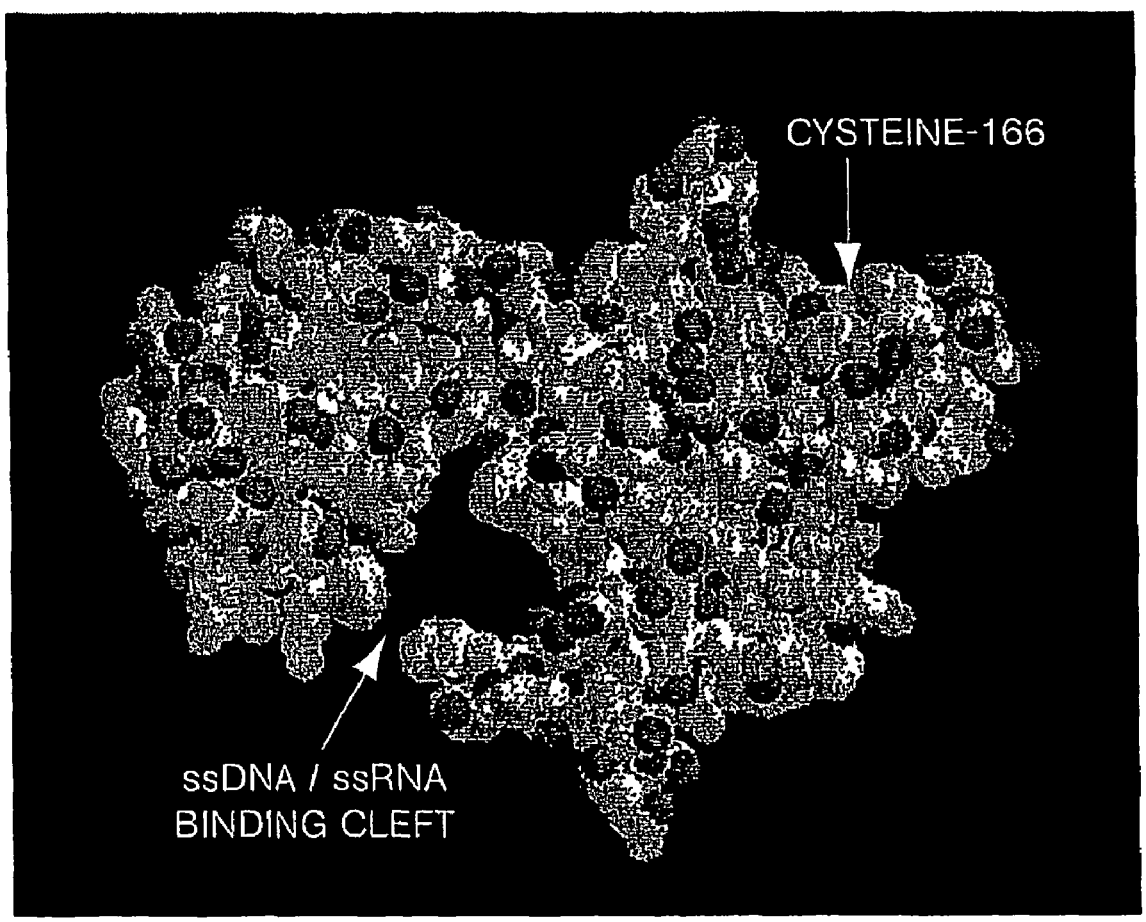
FIG. 2 shows a model of the X-ray crystallographic structure of the single-stranded-binding "core" domain of Bacteriophage T4 gene 32 protein (Gp32; from Shamoo et al., 1995 Nature 376:362-6). Cysteine-166, the residue at which fluorescein is attached is indicated with the upper arrow. The binding cleft for ssDNA and ssRNA is visible at the lower left of the structure as indicated with the lower arrow. Cysteine-166 resides in the single-stranded DNA-binding "core" domain of Gp32.

Other advantages of Gp32F proteins include the fact that its ssDNA and ssRNA binding activities are largely independent of polynucleotide sequence. Therefore, Gp32F proteins will bind strongly to any single-stranded region of sufficient length to support a cooperative cluster of the protein (for example, lengths greater than or equal to about 15-20 nucleotide residues). In addition, Gp32F proteins denatures secondary structures in ssDNA and ssRNA allowing more accurate quantification of these polynucleotides. Gp32F proteins can be prepared in gram quantities from Gp32 protein purified from overexpressing strains of *E. coli*, making industrial scale-up of production practical while minimizing production costs. Additionally, the X-ray crystallographic structure of the ssDNA/ssRNA binding domain of the parent molecule, Gp32 protein, is known (see FIG. 2 and ref. (Shamoo, Y., et al. (1995) *Nature*. 376(6538), 362-6.)), as are details of the thermodynamics and kinetics of Gp32 protein interactions with a variety of single-stranded polynucleotides Kowalczykowski, S. C., et al. (1986) *Biochemistry*. 25(6), 1226-40.). The detailed knowledge of Gp32 protein biochemistry and structure allows intelligent design of experiments and facilitates modifications of Gp32F protein technology via site-directed mutagenesis and/or use of alternative fluorescent molecules for conjugation (see Examples section).

We have discovered that Gp32F protein binds to single-stranded polynucleotides including single-stranded gaps, tails, flaps, loops, or bubbles within double-stranded DNA or RNA molecules (FIG. 3), allowing their detection and localization by fluorescence microscopy. Biomedical research applications of this detection system include, but are not limited to, analyses of nucleic acid. intermediates in: DNA replication; DNA repair pathways including mismatch repair, double-strand break repair, and nucleotide excision repair; homologous genetic recombination; transcription; translation; and RNA processing. Gp32F protein may also. be used to detect regions of unpaired heterology in products of DNA-DNA, RNA-DNA, or RNA-RNA hybridization. In addition, we have identified that Gp32F protein may be soaked into electrophoretic gels to fluorescently stain specifically those DNA or RNA molecules that are single-stranded or that contain single-stranded regions, allowing their identification and/or separation from fully double-stranded polynucleotides. Alternatively, Gp32F protein-induced changes in electrophoretic gel mobility shift coupled with fluorescent detection of the fluorescent molecule tag may be used to identify single-strand containing nucleic acids.

We have also demonstrated the use of Gp32F protein for quantitative spectrofluorometric measurements of DNA and RNA transactions. The fluorescence properties of Gp32F protein make it useful as a coupling system for monitoring DNA and RNA reactions that involve conversions between single- and double-stranded states. Examples of such uses, although not intended to be limiting include: exonucleolytic degradation of DNA or RNA (FIG. 4A), helicase-catalyzed unwinding of double-stranded DNA, RNA, or RNA-DNA hybrids (FIG. 4B), reannealing of complementary single-stranded polynucleotides to form a duplex (FIG. 4C), DNA replication and reverse transcription reactions including replication of primed single-stranded templates and strand displacement DNA synthesis reactions (FIG. 4D), formation of excision gaps during DNA mismatch repair and nucleotide excision repair reactions (FIG. 4E), and homologous genetic recombination-DNA strand exchange reactions and presynaptic filament formation (FIG. 4F).

The Gp32F probes of the invention are highly sensitive. The intensity of the fluorescent molecule (enhanced upon Gp32F binding to polynucleotide) is such that assays as described herein, can even be conducted at Gp32F-protein/polynucleotide concentrations at or below the nanomolar threshold given a spectrofluorometer of sufficient sensitivity.

Methods of the invention also include the use of Gp32F protein for single-molecule enzymology. For example, in embodiments of the invention Gp32F protein may be used as a detection system for single-molecule reactions including, but not limited to: exonuclease reactions (see FIG. 4A), helicase reactions (see FIG. 4B), replication and reverse transcription (see FIG. 4D), and recombination-presynaptic filament formation (see FIG. 4F). In each of these methods, the invention includes embodiments in which individual DNA or RNA molecules are tethered and single-stranded regions are either generated or consumed depending on the nature of the reaction. In these embodiments of the invention, data collection may involve methods including, but not limited to, time-resolved imaging and photon counting.

The methods of the invention also are useful for quantitative analysis of protein-ssDNA and protein-ssRNA interactions. The fluorescence enhancement observed upon Gp32F protein-polynucleotide binding is useful to quantitate other protein-ssDNA or -ssRNA interactions by performing competition experiments in which the displacement of Gp32F protein from the single-stranded polynucleotide is measured as a function of the second protein's concentration, by following the decrease in Gp32F protein signal intensity. Binding parameters for the second protein may be extracted from competition data of this type as described (Kowalczykowski, S. C., et al. (1986) *Biochemistry.* 25(6), 1226-40.). Similar competition assays coupling changes in polynucleotide electrophoretic mobility with loss of Gp32F protein from the complex may be used to determine polynucleotide binding parameters of a second protein.

The compositions and methods of the invention also relate in part to the quantification of single-stranded polynucleotides. For example, the solution concentrations of ssDNA and ssRNA molecules may be measured by titrating a known concentration of Gp32F protein with the nucleic acid and determining the endpoint at which no further fluorescence change takes place. Because the binding site size of Gp32F protein on single-stranded polynucleotides is known, the methods of the invention can be used to calculate the precise concentration of ssDNA or RNA in a solution. The methods of the invention also allow (1) greatly increased sensitivity compared to absorbance measurements of ssDNA/ssRNA concentration; and (2) more accuracy than absorbance or fluorescent ssDNA/ssRNA staining procedures, since the latter two signal types are dependent on the degree of secondary structure present and Gp32F protein can increase accuracy due to its ability to denature secondary structure in single-stranded polynucleotides.

We have synthesized fluorescently labeled GP32 protein by reacting purified Gp32 protein with a fluorescent molecule, for example, 6-iodoacetamidylfluorescein, and have discovered that like unmodified Gp32, Gp32F protein binds specifically, stochiometrically and with high affinity and cooperativity to single-stranded DNA (ssDNA) and RNA (ssRNA) molecules, and exhibits little or no binding to double-stranded DNA or RNA. We have identified a surprising feature of Gp32F protein, which is that upon binding to single-stranded polynucleotides, Gp32F protein exhibits a significant change in fluorescence intensity. The polynucleotide binding and fluorescence properties of Gp32F protein offer several novel practical applications as well as improvements on existing applications, as described below.

As used herein, the term "Gp32F protein" includes wild-type Gp32 protein conjugated to a fluorescent molecule (e.g., fluorescein) at environment-sensitive amino acid position(s) (e.g., cysteine-166) of the Gp32 protein (see FIG. 2), and also includes similarly labeled mutant and variant forms of Gp32 protein. In preferred embodiments, the Gp32 is conjugated at the cysteine-166 position. Alternative Gp32 positions to which a fluorescent molecule can be conjugated to make Gp32F proteins or variants and mutants thereof include, but are not limited to: Serine-195 mutated to cysteine (S195C), Cys-166 mutated to serine (C166S), which can be done simultaneously with the Serine-195 mutation to cysteine, Lysine-51 and Lysine-207. The appropriate derivatives of fluorescent molecules can be used for each of the foregoing amino acids, such as thiol-reactive reagents (e.g., iodoacetamidyl derivatives) for labeling cysteines and amine-selective reagents (e.g., isothiocyante, succinimidyl ester, sulfonyl chloride and/or aldehyde derivatives) for labeling lysines. The foregoing Gp32 modifications can be combined to make modified Gp32 proteins that contain two or more labeled residues, such as a Gp32 mutant protein labeled on Cys-166 and another labeled residue, or a Gp32 mutant labeled on S195C and C166S.

Figure 1:
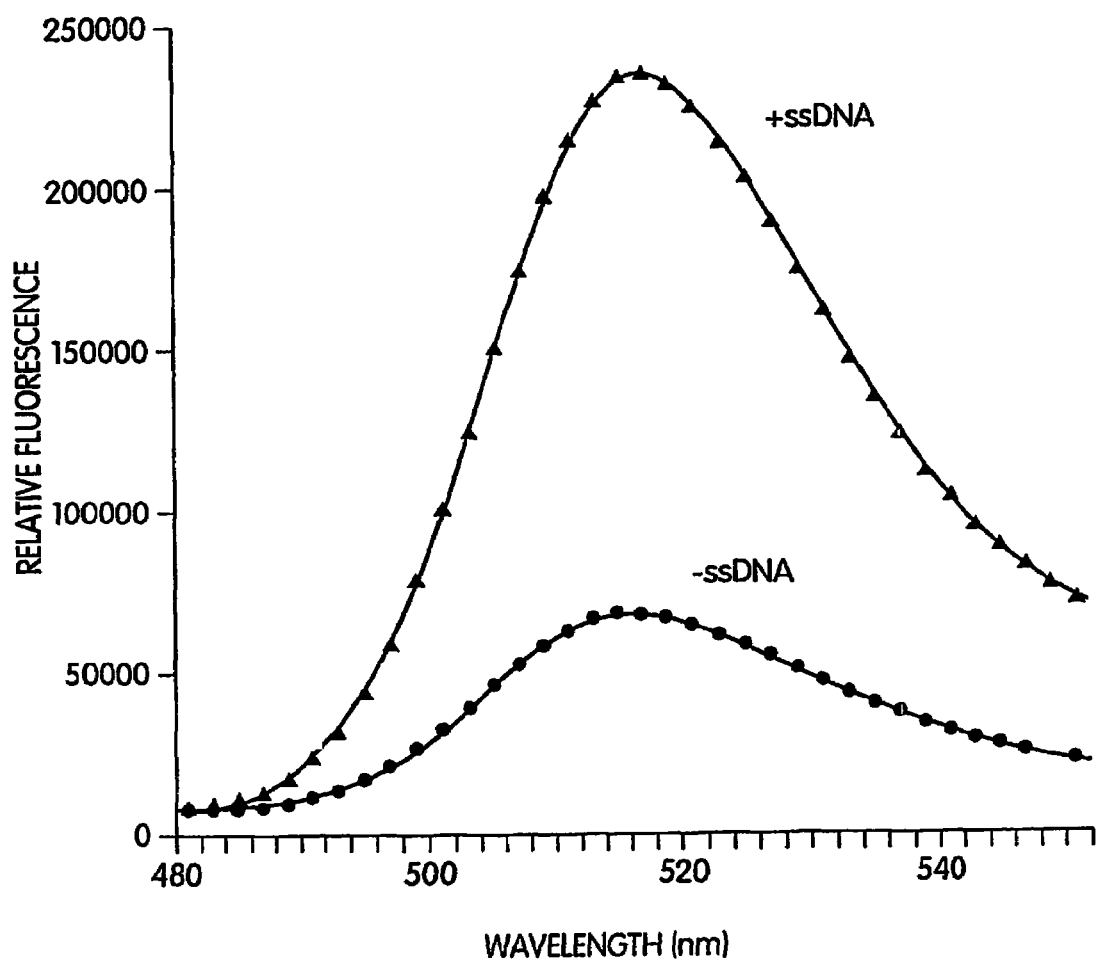
FIG. 1 shows a graph of the fluorescence emission spectrum of Gp32F with and without binding to single-stranded DNA (ssDNA). The excitation wavelength is 465 nm.

The amino acid sequence of wild-type Gp32 protein is provided herein as SEQ ID NO:1, which corresponds to GenBank Accession No. P03695 and the PDB file code is 1GPC. Cysteine-166 is the cysteine in the 166 position in the full-length sequence of Gp32 protein. Upon binding to single-stranded polynucleotides, Gp32F protein exhibits a 2- to 3-fold increase in intensity of fluorescence. For example using fluorescein as the label, the Gp32F protein exhibits a 2- to 3-fold increase in intensity of fluorescence measured at wavelengths of 300 or 465 nm (excitation) and 516 nm (emission), respectively (FIG. 1).

The methods of the invention involve detection of the intensity of the fluorescence of Gp32F protein in various conditions and reactions. As used herein, the term "intensity" means the intensity (e.g., brightness) of the measured fluorescence of the Gp32F protein. As used herein, the term "first intensity" means the intensity of the fluorescence of the Gp32F protein before it is contacted with a single-stranded polynucleotide and as used herein the term "second intensity" is the intensity of the fluorescence of the Gp32F protein after it binds to a single-stranded polynucleotide. The difference between the first intensity and the second intensity is a detectably difference. In preferred embodiments, the second intensity will be at least about 2- to 3-times greater than the first intensity.

The methods of the invention include contacting a sample with a Gp32F protein of the invention and determining the fluorescence of the Gp32F protein that binds to the sample. The methods of the invention include contacting a sample with a Gp32F protein. As used herein, the term "sample" means a solution that may include a polynucleotide, e.g. DNA or RNA, which can be single-stranded, double-stranded, or may include both single- and double-stranded polynucleotides. As used herein, the term "solution" includes reaction mixtures and gels, such as an electrophoresis gel.

In some embodiments, a sample may include tissue, cells, or fragments thereof and/or individual molecules such as double- and single-stranded polynucleotide molecules. As used herein, the term "cells" means cells from a subject (e.g., from a biopsy) and/or cells grown in culture. The cells of the invention may also include plant cells. As used herein, the term "subject" means any mammal, including, but not limited to: humans, non-human primates, cats, dogs, sheep, pigs, horses, cows, rodents such as mice, rats, etc. A subject may also be a non-mammalian vertebrate, an invertebrate, a bacterium, or other organism.

In some embodiments, a sample and/or a Gp32F protein of the invention may be tethered or attached (e.g. covalently) to a surface. Examples of such attachments include, but are not limited to: a cell attached to a slide or a Gp32F protein or a polynucleotide molecule attached to a membrane or to a surface such as glass, plastic, metal, or polystyrene. In some embodiments, the sample or the Gp32F protein may be attached to a bead or dipstick. The attachment of a sample or Gp32F protein to a surface may be a direct covalent attachment or may be an attachment through a linker. An example of use of a linker, though not intended to be limiting, is the attachment of a polynucleotide to a streptavidin-coated polystyrene bead via a biotin molecule attached to the polynucleotide molecule.

A sample may contain a polynucleotide, or may be suspected of containing a polynucleotide. As used herein, the term "polynucleotide" means DNA, RNA, or a DNA-RNA hybrid molecule. The term "single-stranded polynucleotide" means single-stranded DNA (ssDNA) or single-stranded RNA (ssRNA) and includes single-stranded stretches of DNA or RNA. Single-stranded DNA or single-stranded RNA molecule may be single-stranded along its entire length, (e.g. ssDNA or ssRNA, FIG. 3), or may be a single-stranded inclusion in a double-stranded DNA or RNA molecule. Examples of such single-stranded inclusions are provided in FIG. 3, and include, but are not limited to single-stranded gaps, single-stranded tails, single-stranded flaps, single-stranded loops, and single-stranded bubbles.

As used herein, the term "determining the fluorescence" means measuring the fluorescence. In some embodiments, this involves measuring the presence of fluorescence in contrast to zero fluorescence. In certain embodiments, this includes measuring the amount of fluorescence. In some embodiments, this includes measuring the change of intensity of the fluorescence. The measurement can be done with an optical reading method. Optical methods of measuring fluorescence are well known by those of ordinary skill in the art and include, but are not limited to, visualization, spectrophotometry, fluorimetry, microscopy, video microscopy, digital microscopy, digital imaging, and fluorescence plate reader methods. Some embodiments of the invention include high-throughput optical screening methods, time-resolved imaging, and/or photon counting methods. These and other optical fluorescence-detection means can be utilized in the methods of the invention. The application of these and other optical detection methods in the methods of the invention will be understood by those of ordinary skill in the art.

If a sample that contains a single-stranded polynucleotide is contacted with a Gp32F protein of the invention, the fluorescence intensity of the Gp32F protein can be detected using a detection method described herein. It will be understood by those of ordinary skill in the art, that the change in intensity may be a change from a control level or from a level measured in a sample at a previous or later time point. One example of a control level of fluorescence is the level of fluorescence of a Gp32F protein that has not been contacted with a single-stranded polynucleotide. Another example of a control level of fluorescence is the level of fluorescence of a Gp32F protein that has been contacted with a double-stranded polynucleotide. Still another example of a control level of fluorescence is the level of fluorescence of a Gp32F protein that has been contacted with an fully single-stranded polynucleotide (e.g., when measuring decreases in Gp32F binding and fluorescence). In some embodiments, the control level can be used to compare with the level of fluorescence after a Gp32F protein is contacted with a sample. A change (e.g. increase or decrease) in the intensity of the fluorescence after contact with the sample indicates that there is single-stranded polynucleotide in the sample. The comparison of a control intensity with a sample intensity can also be used to quantitate an amount of single-stranded polynucleotide in a sample. For example, control and test samples can be electrophoresed on a gel, and the gel can be contacted with Gp32F protein (e.g. soaked in a staining solution containing Gp32F protein). The amount of single-stranded polynucleotide in the test sample can then be determined by comparing the intensity of the control and test sample fluorescent intensities.

The invention provides methods to quantitate the amount of single-stranded polynucleotides in a sample. These methods involve contacting a sample with Gp32F protein to determine the amount of single-stranded polynucleotide. The methods are based in part of the fact that the binding site of Gp32F protein on ssDNA is eight nucleotide residues per protein monomer, which is also the binding site size for unlabeled Gp32 protein. Knowing this binding site size, and the starting concentration of Gp32F protein, the single-stranded polynucleotide concentration can be determined by titrating the Gp32F protein with a single-stranded polynucleotide solution until an endpoint is reached (i.e. fluorescence no longer increases). The endpoint indicates the volume of the single-stranded polynucleotide solution containing an amount of ssDNA/ssRNA nucleotide residues equal to eight times the concentration of Gp32F protein, thus indicating the concentration. Variations of this method include titrating a fixed amount of ssDNA/ssRNA with Gp32F protein until an endpoint is reached (slope of fluorescence increase decreases to equal slope of protein-only control). Using this method, the endpoint yields ssDNA/ssRNA concentration via a similar calculation. Additionally, a fixed volume of single-stranded solution can be added to a known amount of Gp32F protein, the fluorescence measured, and the single-stranded concentration can be interpolated by comparison to a curve of known standard concentrations.

In some embodiments of the invention, a change (increase or decrease) in the intensity of fluorescence of a Gp32F protein over time can be determined, and additionally may be compared to a control intensity of fluorescence of the Gp32F protein. The identification of changes in fluorescence intensity over time in a reaction mixture or other sample allows reaction features such as timing and the extent of polynucleotide structure changes to be monitored. For example, in reaction mixtures of DNA and RNA transactions, such as those illustrated in FIG. 4A-FIG. 4F, the comparison of fluorescence intensity at different time points and against a control fluorescence intensity level can be made. The comparison allows quantitation of the amount of single-stranded polynucleotide sequences in the reaction, and also provides information on the progress and/or status of the polynucleotide transactions.

In some embodiments of the invention, the Gp32 protein in the Gp32F protein compound is a mutant form of Gp32 protein. In one embodiments of mutant Gp32F protein, for example, the fluorescent molecule may be conjugated to cysteine-166, based on the amino acid positions in the wild-type sequence. For example, in a mutant Gp32 protein that is a truncated form of wild-type Gp32 protein, the cysteine in the mutant that corresponds to the wild-type cysteine-166 mutant will be conjugated to the fluorescent molecule. The identification of the corresponding cysteine in mutant forms of Gp32 protein can be based on the comparison of the mutant and wild-type sequences and such comparisons can be done using routine methods known to those of ordinary skill in the art. In some embodiments, in a mutant Gp32F, the fluorescein may be conjugated to an amino acid that is not cysteine 166, as long as the Gp32F retains functional activity. As described above, in some embodiments, the fluorescent molecule is conjugated to an amino acid of a wild-type or mutant or variant Gp32 in a position other than the cysteine-166 position.

The invention also relates in part to the conjugation of different fluorescent probes at environment-sensitive positions that result in an increase in fluorescence upon single-stranded polynucleotide binding of Gp32 protein or mutant Gp32 protein (such as cysteine-166). This provides a different wavelength range of fluorescence detection, e.g., for use in a double-labeling experiment or to establish a donor-acceptor pair for fluorescence resonance energy transfer (FRET) experiments. Also, Gp32 protein or mutant Gp32 protein may be conjugated to a more environment-sensitive fluorescent probe than fluorescein at cysteine-166, which yields a larger change in fluorescence upon polynucleotide binding. Fluorescent molecules that can be used to label Gp32 protein and/or mutant Gp32 proteins include, but are not limited to: BODIPY maleimides, iodoacetamides and methyl bromides; Alexa Fluor maleimides; fluorescein 5- and 6-isomer maleimides and methyl bromides; Oregon Green isothiocyanates and maleimides; tetramethylrhodamine 5- and 6-isomer iodoacetamides and maleimides; Rhodamine Red maleimides; Texas Red bromoacetamides and maleimides; pyridyloxazole maleimides; benzoxadiazole derivatives including NBD halides and iodoacetamides, SBD; Lucifer Yellow iodoacetamide; stilbene iodoacetamides and maleimides; coumarin maleimides and iodoacetamides, i.e. MDCC, IDCC, and others; napthalene derivatives , i.e. acrylodan, badan, IAANS, MIANS, IAEDANS, and Dansyl; aziridine; dapoxyl derivatives, i.e. dapoxyl (2-bromoacetamidly)sulfonamide; pyrene maleimides and iodoacetyl derivatives; and monobromo- and monochlorobimanes.

In some aspects of the invention, the Gp32F proteins include functional analogs, derivatives, variants, mutants, and fragments of the Gp32F protein. For example, functional analogs, derivatives, variants, mutants, and fragments of the Gp32F protein can be made, for example, to enhance a property of a compound, such as stability. Functional analogs, derivatives, variants, mutants, and fragments of the Gp32F protein may also be made to provide a novel activity or property to a Gp32F protein, for example, to enhance detection. In some embodiments of the invention, modifications to a Gp32F protein molecule of the invention can be made to the structure or side groups of the compound and can include deletions, truncations, substitutions, and additions of atoms, or side groups. Alternatively, modifications can be made by cleavage, addition of a linker molecule, addition of an additional detectable moiety, such as biotin, fluorescent label, or radioactive label, or substitution of one atom for another and the like. Functional analogs, derivatives, variants, mutants, and fragments of the Gp32F protein that retain the single-stranded binding activity of the Gp32F protein molecule, respectively, also can be used in accordance with the invention.

The invention also includes the use of orthologs of the Gp32F protein as well as mutants and variants thereof as described herein. Thus, for example, Gp32F protein analogs from other bacteriophages can be used in the methods and compositions of the invention.

According to some aspects of the invention, Gp32F proteins include variants or mutants of Gp32 proteins, for example the Gp32 mutant proteins described in the Examples section. Thus, the Gp32F proteins of the invention include proteins that are variants or mutants of the wild-type Gp32 protein, provided that the variant or mutant Gp32F protein exhibits the Gp32F functional activity. As used herein, a Gp32F functional activities include to the ability of a Gp32F to bind to single-stranded polynucleotide molecules as described herein, and/or the change in intensity of the fluorescence upon binding of the Gp32F protein compound to a single-stranded polynucleotide. The ability of a mutant or variant form of a Gp32F protein to have a Gp32F protein functional activity can be determined by measuring its ability to bind to single-stranded polynucleotides and/or measuring the intensity of the fluorescence of the Gp32F protein using, for example, the assays described in the Examples.

Mutant Gp32F protein molecules of the invention may include an amino acid sequence which is identical to Gp32F protein (also referred to herein as wild-type Gp32F protein) with the exception that the sequence has 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more mutations, e.g., deletions, additions or substitutions, as long as the mutant Gp32F protein exhibits some of the functional activity of Gp32F protein. In some instances, a mutant Gp32F protein may have 100% of the functional activity of Gp32F protein and in other instances may exhibit enhanced Gp32F protein activity and thus may have more than 100% of the functional activity of Gp32F protein. In some embodiments, the mutant Gp32F protein may have less than 100% of the functional activity of Gp32F, yet still have greater than zero functional activity.

In some embodiments a mutant Gp32F may comprise a truncated form of Gp32. Truncated Gp32 can be full-length Gp32 minus 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277 278, 279, 280, 281, 282, 283, 284, 285, 286, 287, 288, 289, 290, or more amino acids. The eliminated amino acids may be from either and/or both the N-terminus or the C-terminus of the Gp32 sequence, or from internal portions of the Gp32 protein. The assays provided herein can be used to ascertain the level of Gp32F protein activity in a truncated form of Gp32F protein, to determine its single-stranded binding and fluorescence characteristics for use in the methods of the invention.

Gp32 protein and mutant Gp32 proteins of the invention can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Short polypeptides also can be synthesized chemically using well-established methods of peptide synthesis.

Thus, as used herein with respect to proteins, "isolated" means separated from its native environment and present in sufficient quantity to permit its identification or use. Isolated, when referring to a protein or polypeptide, means, for example: (i) selectively produced by expression of a recombinant nucleic acid or (ii) purified as by chromatography or electrophoresis. Isolated proteins or polypeptides may, but need not be, substantially pure. The term "substantially pure" means that the proteins or polypeptides are essentially free of other substances with which they may be found in nature or in vivo systems to an extent practical and appropriate for their intended use. As used herein, the terms "proteins" and "polypeptides" may be used interchangeably. Substantially pure proteins may be produced by techniques well known in the art. Because an isolated protein may be admixed with a acceptable carrier in a preparation or a solution, the protein may comprise only a small percentage by weight of the preparation. The protein is nonetheless isolated in that it has been separated from the substances with which it may be associated in living systems, e.g. isolated from other proteins.

The invention also includes fragments of a Gp32F protein, for example, fragments that retain all of part of the functional activity of a Gp32F protein. Fragments of a protein preferably are those fragments which retain a distinct functional capability of the protein. Functional capabilities that can be retained in a fragment of a protein include single-stranded polynucleotide binding activity and/or the shift in fluorescence upon single-stranded polynucleotide binding, and enzymatic activity.

Those skilled in the art are well versed in methods for selecting unique amino acid sequences, typically on the basis of the ability of the fragment to selectively distinguish the sequence of interest from non-family members. A comparison of the sequence of the fragment to those on known databases typically is all that is necessary.

The invention embraces variants of the Gp32F protein described herein. As used herein, a "variant" of a Gp32F protein is a protein that contains one or more modifications to the primary amino acid sequence of a Gp32F protein. Modifications that create a Gp32F protein variant can be made to a Gp32F protein 1) to produce, increase, reduce, or eliminate an activity of the Gp32F protein; 2) to enhance a property of the Gp32F protein, such as protein stability in an expression system or the stability of protein-protein binding; 3) to provide a novel activity or property to a Gp32F protein, such as addition of an antigenic epitope or addition of a detectable moiety; or 4) to provide equivalent or better binding to single-stranded polynucleotide molecule. Modifications to a Gp32F protein are typically made to the nucleic acid molecule which encodes the protein, and can include deletions, point mutations, truncations, amino acid substitutions, and additions of amino acids or non-amino acid moieties. Alternatively, modifications can be made directly to the protein, such as by cleavage, addition of a linker molecule, addition of an additional detectable moiety, such as biotin or a second fluorescent molecule, and the like. Modifications also embrace fusion proteins comprising all or part of the Gp32F amino acid sequences. One skilled in the art will be familiar with methods for predicting the effect on protein conformation of a change in protein sequence, and can thus "design" a variant Gp32F polypeptide according to known methods. One example of such a method is described by Dahiyat and Mayo in *Science* 278:82-87, 1997, whereby proteins can be designed de novo. The method can be applied to a known protein to vary only a portion of the protein sequence. By applying the computational methods of Dahiyat and Mayo, specific variants of a Gp32F protein can be proposed and tested to determine whether the variant retains a desired conformation.

In general, variants include Gp32F proteins which are modified specifically to alter a feature of the protein unrelated to its desired physiological activity. For example, cysteine residues can be substituted or deleted to prevent unwanted disulfide linkages. Similarly, certain amino acids can be changed to enhance expression of a Gp32F protein by eliminating proteolysis by proteases in an expression system (e.g., dibasic amino acid residues in yeast expression systems in which KEX2 protease activity is present).

Mutations of a nucleic acid molecule that encode a Gp32 protein preferably preserve the amino acid reading frame of the coding sequence, and preferably do not create regions in the nucleic acid which are likely to hybridize to form secondary structures, such a hairpins or loops, which can be deleterious to expression of the variant protein.

Mutations can be made by selecting an amino acid substitution, or by random mutagenesis of a selected site in a nucleic acid which encodes the protein. Variant proteins are then expressed and tested for one or more activities of Gp32 to determine which mutation provides a variant protein with the desired properties. Further mutations can be made to variants (or to non-variant Gp32F proteins) which are silent as to the amino acid sequence of the protein, but which provide preferred codons for translation in a particular host. The preferred codons for translation of a nucleic acid in, e.g., *E. coli*, are well known to those of ordinary skill in the art. Still other mutations can be made to the noncoding sequences of a Gp32 gene or cDNA clone to enhance expression of the protein. The activity of variants of Gp32F proteins can be tested by cloning the gene encoding the variant Gp32 protein into a bacterial or mammalian expression vector, introducing the vector into an appropriate host cell, expressing the variant Gp32 protein, adding the label to the protein, and testing for a functional capability of the Gp32F protein as disclosed herein. Preparation of other variant proteins may favor testing of other activities, as will be known to one of ordinary skill in the art.

The skilled artisan will also realize that conservative amino acid substitutions may be made in Gp32F proteins to provide functional variants of the foregoing proteins, i.e, the variants with the functional capabilities of the Gp32F proteins. As used herein, a "conservative amino acid substitution" refers to an amino acid substitution that does not alter the relative charge or size characteristics of the protein in which the amino acid substitution is made. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

For example, upon determining that a peptide derived from a Gp32F protein possesses single-stranded polynucleotide binding activity, one can make conservative amino acid substitutions to the amino acid sequence of the peptide. The substituted peptides can then be tested for one or more of the above-noted functions, in vivo or in vitro. These variants can be tested for improved stability and binding properties.

Functional variants of Gp32F proteins, i.e., variants of proteins which retain the function of the Gp32F proteins, can be prepared according to methods for altering polypeptide sequence known to one of ordinary skill in the art such as are found in references which compile such methods, e.g. *Molecular Cloning: A Laboratory Manual*, J. Sambrook, et. al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Conservative amino-acid substitutions in the amino acid sequence of Gp32F proteins to produce functional variants of Gp32F proteins typically are made by alteration of the nucleic acid molecule encoding a Gp32F protein. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding a Gp32 protein. Where amino acid substitutions are made to a small unique fragment of a Gp32F protein, the substitutions can be made by directly synthesizing the peptide. The activity of functional variants or fragments of Gp32F protein can be tested by cloning the gene or transcript that encodes the altered Gp32 protein into a bacterial, mammalian, or insect cell expression vector, introducing the vector into an appropriate host cell, expressing the altered Gp32 protein, adding the label to the protein, and testing for a functional capability of the Gp32F proteins as disclosed herein.

The invention as described herein has a number of uses, some of which are described elsewhere herein. First, the invention permits isolation of the Gp32F protein molecules. A variety of methodologies well known to the skilled practitioner can be utilized to obtain isolated Gp32F protein molecules. The Gp32 protein may be purified from cells that naturally produce the protein by chromatographic means or immunological recognition. Alternatively, an expression vector may be introduced into cells to cause production of the protein. In another method, mRNA transcripts may be microinjected or otherwise introduced into cells to cause production of the encoded protein. Translation of mRNA in cell-free extracts such as the reticulocyte lysate system also may be used to produce polypeptide. Those skilled in the art also can readily follow known methods for isolating Gp32 proteins. These include, but are not limited to, HPLC, size-exclusion chromatography, ion-exchange chromatography, and immune-affinity chromatography. Following isolation, the Gp32 can be labeled with the detectable label using the methods described herein, and tested for single-stranded polynucleotide binding activity. Those skilled in the art will also be able to utilize recombinant Gp32F protein to determine the crystal structure of the Gp32F protein variants.

Using the structures of the Gp32 protein and mutant Gp32 proteins disclosed herein, one of ordinary skill in the art is enabled to make predictions of structural motifs and sequence variations for analogs, variants, derivatives, and/or fragments that possess similar functions of the Gp32F and mutant Gp32F compounds disclosed herein. Using structural and sequence motifs as search, evaluation, or design criteria, one of ordinary skill in the art is enabled to identify compounds (functional variants of the Gp32F protein and mutant Gp32F proteins) that have a reasonable likelihood of possessing the modulatory function of the compounds disclosed herein. These compounds may be synthesized and tested for activity as described herein.

The invention in part also involves the use of methods to determine the functional activity of Gp32F protein and mutant Gp32F proteins described herein. Although not intended to be limiting, an example of a method with which the ability of a Gp32F protein and mutant Gp32F proteins to bind to single-stranded polynucleotides can be tested in an in vitro assay system as described herein. As used herein, the term "fluorescent label" means a label or marker that fluoresces and can be detected using an optical or visual means, and includes, but is not limited to fluorescent, bioluminescent, luminescent labels, examples of which are listed elsewhere herein. In some embodiments, a Gp32F protein or mutant Gp32F protein may further comprise a second detectable label. A second detectable label of the invention may include a chromophore or may include a radiolabel, or other label detectable optically or using other known methods (including fluorescent molecules that fluoresce at different wavelengths than a first detectable label).

Assays, such as those described herein, may be used to determine the functional activity of Gp32F protein and mutant Gp32F proteins of the invention. Such assays may be used to compare levels single-stranded polynucleotide binding of Gp32F protein with levels determined for variant or mutant Gp32F proteins. Such methods may also be utilized to determine the activity status of analogs, variants, derivatives, and fragments as agents that can be used to determine the level of single-stranded polynucleotide in a sample. Once a Gp32F protein or mutant Gp32F protein is verified as binding to single-stranded polynucleotides, further biochemical and molecular techniques may be used to elucidate the specific roles that these molecules play in the process of single-stranded polynucleotide binding.

The invention also relates in part to the use of Gp32F proteins in diagnostic methods such as methods with which to stage cancer and tumors, and methods to monitor the efficacy of treatments for disorders and diseases, for example, cancer. In some embodiments, a tissue or cell sample from a subject may be contacted with a Gp32F protein of the invention and the structure of the DNA and/or RNA may be determined. For example, a Gp32F protein will bind to regions of damaged DNA, thus if DNA in a subject's cells has been damaged, e.g. in a disease-related or treatment-induced process, a Gp32F protein will indicate the presence of the damage in a cell or tissue sample from the subject. Thus, the single-stranded detection methods of the invention are useful to diagnose disorders such as cancer or other disorders characterized by abnormal DNA or RNA or characterized by damage to DNA or RNA.

In addition, the diagnostic methods of the invention can be used to monitor polynucleotide characteristics in cells and tissues in a subject. For example, in a subject undergoing treatment for a disorder, tumor and/or tumor-free samples obtained from the subject at various times may be contacted with the Gp32F protein of the invention and the amount of damage to DNA in the cells and tissues can be quantitated. The methods may be useful to assess damage in cells that results from causes that include, but are not limited to: therapeutic treatments, environmental factors (e.g. toxins, UV exposure, etc.), disease onset, progression, or regression, and injury. Thus, the single-stranded polynucleotide detection methods of the invention can be used as diagnostic methods to determine changes in cell DNA and RNA status over time, under different conditions, and under various treatment regimens.

The invention also provides a kit comprising one or more containers comprising one or more of the Gp32 and/or mutant Gp32 proteins of the invention, a fluorescent molecule and/or other detectable label for labeling the Gp32 or mutant Gp32, and/or formulations of the invention. The kit may also include instructions for the labeling of Gp32 and/or mutant Gp32 compounds with the fluorescent molecule and/or other detectable label, and instructions for the use of the Gp32F and/or mutant Gp32F proteins or formulations of the invention for to bind to and quantitate single-strand polynucleotides.

In some embodiments of the invention, a kit may include Gp32F and/or mutant Gp32F and or instructions for the use of the compounds to bind to and quantitate single-stranded polynucleotides.

The invention will be more fully understood by reference to the following examples. These examples, however, are merely intended to illustrate the embodiments of the invention and are not to be construed to limit the scope of the invention.

EXAMPLES

Example 1

Labeling Gp32 with 6-IAF (6-iodoacetamidofluorescein):

Gp32 protein was labeled with 6-IAF using the following protocol.
1. 6-IAF (6-iodoacetamidofluorescein)
    a). Thiol-reactive reagent; $C_{22}H_{14}NO_6$ with M.W. 515.26.
    b). Stock preparation—6 mg 6-IAF dissolved in 1 ml DMSO with molar concentration $1.164 \times 10^{-2}$ M kept at −20 degrees C.
2. Labeling buffer was made by combining:
    20 mM Tris-HCl, pH 7.1
    150 mM NaCl
    10% Glycerol
3. A Labeling procedure was performed with all steps in the dark.
    a). Gp32 dialysis
    Dialyzed 3 mg Gp32 (or any amount of Gp32) in the labeling buffer 2×2 Liters overnight at 4 degrees C.
    b). Dye preparation
    A solution of 1 mM 6-IAF was prepared in labeling buffer.
    c). Labeling Gp32
    The $A_{280}$ of Gp32 was measured after dialysis to calculate the accurate molar concentration of the protein, then 1 mM 6-IAF was added drop by drop into the protein with a molar ratio of Gp32/6-IAF=1/2 at 4° C. The labeled protein was incubated overnight at 4° C. with slow rocking.
    d). Eliminating free dye
    100mM BME (2-mercaptoethanol) was prepared with the labeling buffer, then BME was added drop by drop into the labeled protein with a molar ratio of Gp32/BME=1/4. The solution was incubated at 4 degrees C. for 3 hours with shaking.
    e). Removal of free BME
    The labeled protein was dialyzed in the labeling buffer thoroughly 3×2 liters overnight at 4 degrees C. to get rid of BME, then the labeled protein was dialyzed in storage buffer (20 mM Tris-Hcl, pH 8.1, 150 mM NaCl, 10% glycerol, 10 µM BME) overnight at 4° C., then it was frozen in liquid nitrogen and stored at −80° C.
4. The labeling of Gp32 was checked by SDS-PAGE
    The labeled protein was run on a 15% SDS-PAGE gel to confirm a yellow band (under hand-held UV lamp) of Gp32F before the gel was dyed with Coomassie stain.
5. Determining the labeling efficiency of Gp32F.
    a). The extinction coefficient of 6-IAF was calculated in the labeling buffer at 492 nm and 280 nm.

$E_{492nm}(6\text{-}IAF)=1.037\times10^5\,M^{-1}\,cm^{-1};$ $E_{492nm}(6\text{-}IAF)=3.18\times10^4\,M^{-1}\,cm^{-1}.$ b).The $A_{492}$ of the Gp32F was measured. The labeling ratio was calculated via this formula:

moles of 6-IAF/moles of the Gp32 protein=$A_{492nm}$ (Gp32F)×$M.W$(Gp32)/$E_{492nm}$(6-IAF)×concentration of Gp32(mg/ml)

6. Determining the concentration of Gp32F.
    a). The contribution at $A_{280}$ by the 6-IAF was calculated.

$A_{280nm}$(6-IAF)=$A_{492nm}$(Gp32F)×$E_{280nm}$(6-IAF)/$E_{492nm}$(6-IAF)

b). Measure the total $A_{280}$ of the Gp32F.

Concentration of Gp32F=[$A_{280nm}$(total)−$A_{280nm}$(6-IAF)]/$E_{280nm}$(Gp32)

Note: $E_{280nm}$(Gp32)=41306 $M^{-1}\,cm^{-1}$

Example 2

Modifications of Gp32F System Involving Known Mutations of T4 Gene 32 Protein

Figure 5:
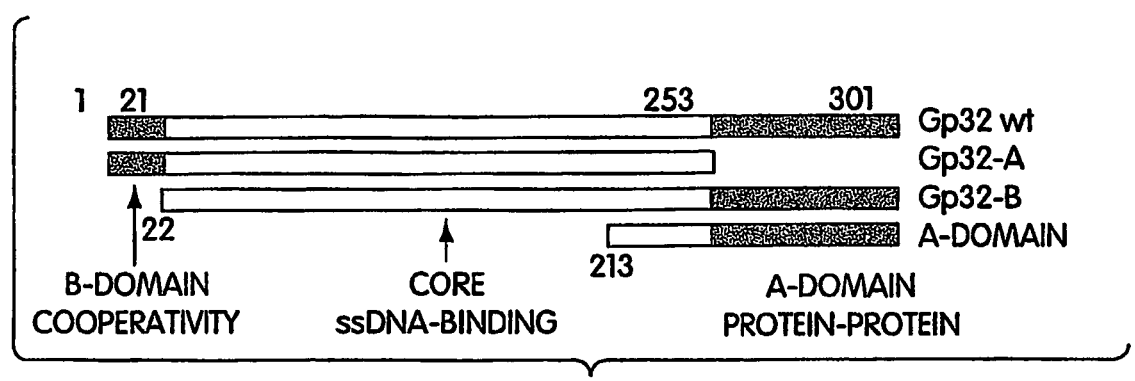
FIG. 5 is a schematic diagram of structures of selected Gp32 truncations. The numbers correspond to the amino acid numbers in the wild-type Gp32 protein (see SEQ ID NO:1).

A) We performed characterization studies of several known mutated forms of T4 gene 32 protein (Gp32). These include truncation mutants Gp32-A, Gp32-B, A-domain, and CORE (amino acid residues 22-253), shown schematically in FIG. 5. Of these, Gp32-A, Gp32-B, and CORE retained the ability to bind to single-stranded polynucleotides. We have also performed characterization studies of point mutations located in the extreme N-terminus of Gp32 (the "B-domain", required for cooperative binding to polynucleotides) (see Villemain et al. *J. Biol. Chem.* 275:40:31496-31502, 2000). These point mutants involve single amino acid substitutions of residues Lysine-3 (K3) and Arginine-4 (R4) in Gp32, including R4K (arginine→lysine), R4Q (arginine→glutamine), R4T (arginine→threonine), R4G (arginine→glycine), and K3A (lysine→alanine).

Collectively, these Gp32 truncation and point mutants provide a set of reagents with a wide range of affinities for single-stranded polynucleotides. The hierarchy of relative affinities for ssDNA/ssRNA was found to be as follows:

Gp32-A>R4K≧Gp32 wild-type>K3A≧R4Q>R4T>R4G>>Gp32-B>CORE    (Scheme 1)

Figure 6:
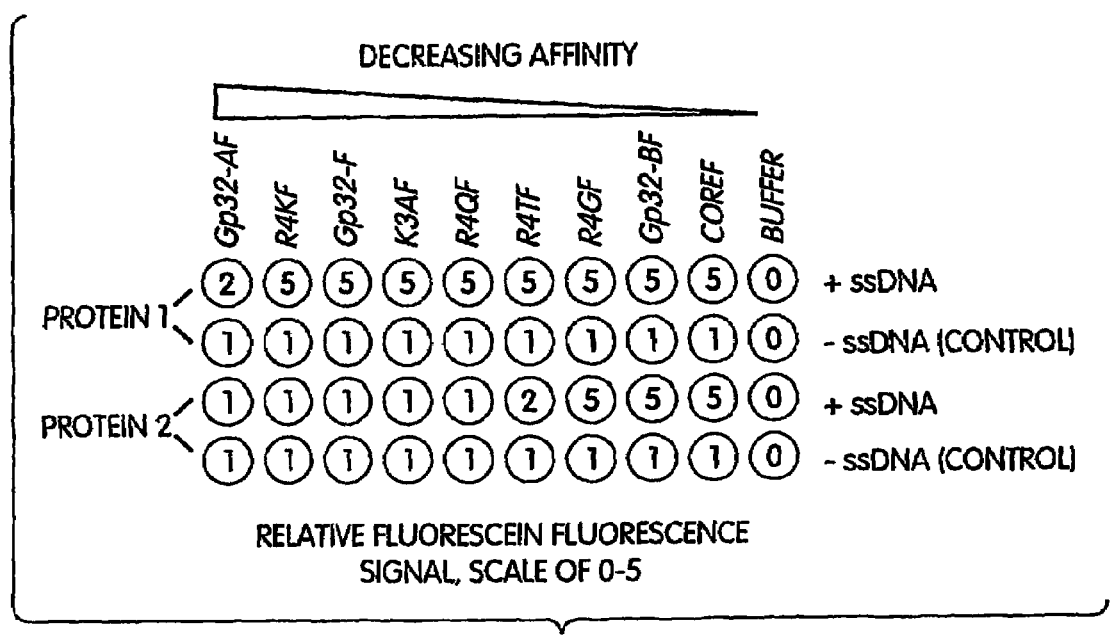
FIG. 6 is a schematic diagram of an assay using mutated Gp32F derivatives to approximate the affinity of other proteins for single-stranded DNA. Under the buffer conditions used, ad assuming Protein 1 and 2 concentrations equimolar with respect to Gp32F derivative-ssDNA complex, the experiment demonstrated that (1) Protein 1 has affinity for ssDNA approximately equal to that of Gp32-AF (i.e. enhanced affinity range), and (2) that Protein 2 has affinity for ssDNA that is approximately equal to that of R4TF (i.e. medium affinity range).

From left to right within this hierarchy, the apparent binding constant for polynucleotide binding decreased by a factor of $10^4$-$10^5$. All of the mutants shown in Scheme 1 contain amino acid residue Cysteine-166, the site of fluorescein attachment in Gp32F. Fluorescein or other fluorescent groups are attached to the same location on each Gp32 mutant using thiol-selective chemistry. Thus, a set of systematically mutated Gp32F fluorescent conjugates are constructed and those with desirable polynucleotide binding properties are selected for use in various experiments, e.g.—enhanced affinity conjugates (Gp32-AF, R4KF), high affinity conjugate (wild-type Gp32F), medium affinity conjugates (K3AF, R4QF, R4TF, R4GF), and low affinity conjugates (Gp32-BF, COREF). This dramatically extends the dynamic range of certain Gp32F-based assays. For example, the approximate binding constant of any protein for ssDNA or ssRNA can be rapidly established by comparing its ability to displace different Gp32F mutant forms from the polynucleotide, as shown schematically in FIG. 6. Displacement of a Gp32 derivative from ssDNA by another protein would decrease fluorescein fluorescence to background (control) levels. The mutant forms of Gp32F described herein are also useful in other assays described herein and allow selection of an appropriate Gp32F mutant derivative to fit the affinity needs of an experiment.

B) Additional sites in Gp32 which can be targeted for fluorescent conjugation, and which can yield changes in fluorescence intensity upon polynucleotide binding, are inferred from the X-ray crystal structure of the CORE domain of Gp32 (pdb file code 1GPC): Residue Serine-195 (Ser195) is located near Cys-166 on the surface of Gp32's CORE domain, and is likely to be affected by the same conformational change affecting Cys-166 upon polynucleotide binding. Ser195 is conservatively mutated to cysteine without loss of protein function. Such an S195C mutation creates a new site for covalent modification with thiol-reactive fluorescent reagents including 6-iodoacetamidylfluorescein and others fluorescent labels listed above herein. Simultaneously, Cys-166 can be conservatively mutated to serine to create a Gp32-S195C/C166S mutant with a single reactive thiol for site-specific labeling. (The three remaining cysteines in Gp32 are involved in zinc ion coordination and are essentially non-reactive under conditions employed for fluorescent labeling.) It is expected that fluorescent molecules conjugated to the engineered Cys195 in this mutant would undergo an environmental change upon ssDNA/ssRNA binding resulting in change fluorescence intensity.

Additional Sites for Labeling Gp32 Protein

Other sites for fluorescent labeling of Gp32 include Lysine-51 and Lysine-207. These residues occupy the same region of the surface of Gp32 as do Cys-166 and Ser-195, so fluorescent molecules attached at these sites undergo environmental change, and therefore fluorescence intensity changes upon protein binding to ssDNA/ssRNA. These lysine residues are labeled with amine-selective derivatives of fluorescent molecules provided herein, including isothiocyanate, succinimidyl ester, sulfonyl chloride, and/or aldehyde derivatives of BODIPY dyes, Alexa Fluor dyes, Fluoresceins, Oregon Green dyes, Rhodamine derivatives, Texas Red dyes, Coumarin dyes Napthalene derivatives, Dansyl derivatives, Pyrene derivatives, Pyridyloxazoles Benzoxadiazoles. Lucifer Yellow, and Stilbene. Mutagenesis of other lysine residues in Gp32 are carried out as needed to ensure site-specific labeling at either Lys51 or Lys207.

Example 3

A High-throughput Assay for Protein-ssDNA Interactions.

We have developed a high-through put assay for protein-ssDNA interactions based on Gp32F displacement.

A. Plate Reader Experiment.

The five wells in 96-well plate were chosen and named as A. B. C. D. E. A sixth well (not shown) contained a buffer blank for background, the signal from which was subtracted from all data.

A—Containing 0.5 µM Gp32F

B—Containing 0.5 µM Gp32F plus 4 µM M13 mp18 ssDNA

C—Containing 0.5 µM Gp32F plus 6 µM UvsX and 1 mM ATP

D—Containing 0.5 µM Gp32F plus 4 µM M13 mp18 ssDNA, 6 µM UvsX, and 1 mM ATP

E—Containing 0.5 µM Gp32F plus 4 µM M13 mp18 ssDNA and 700 mM NaCl (final concentration)

Figure 8:
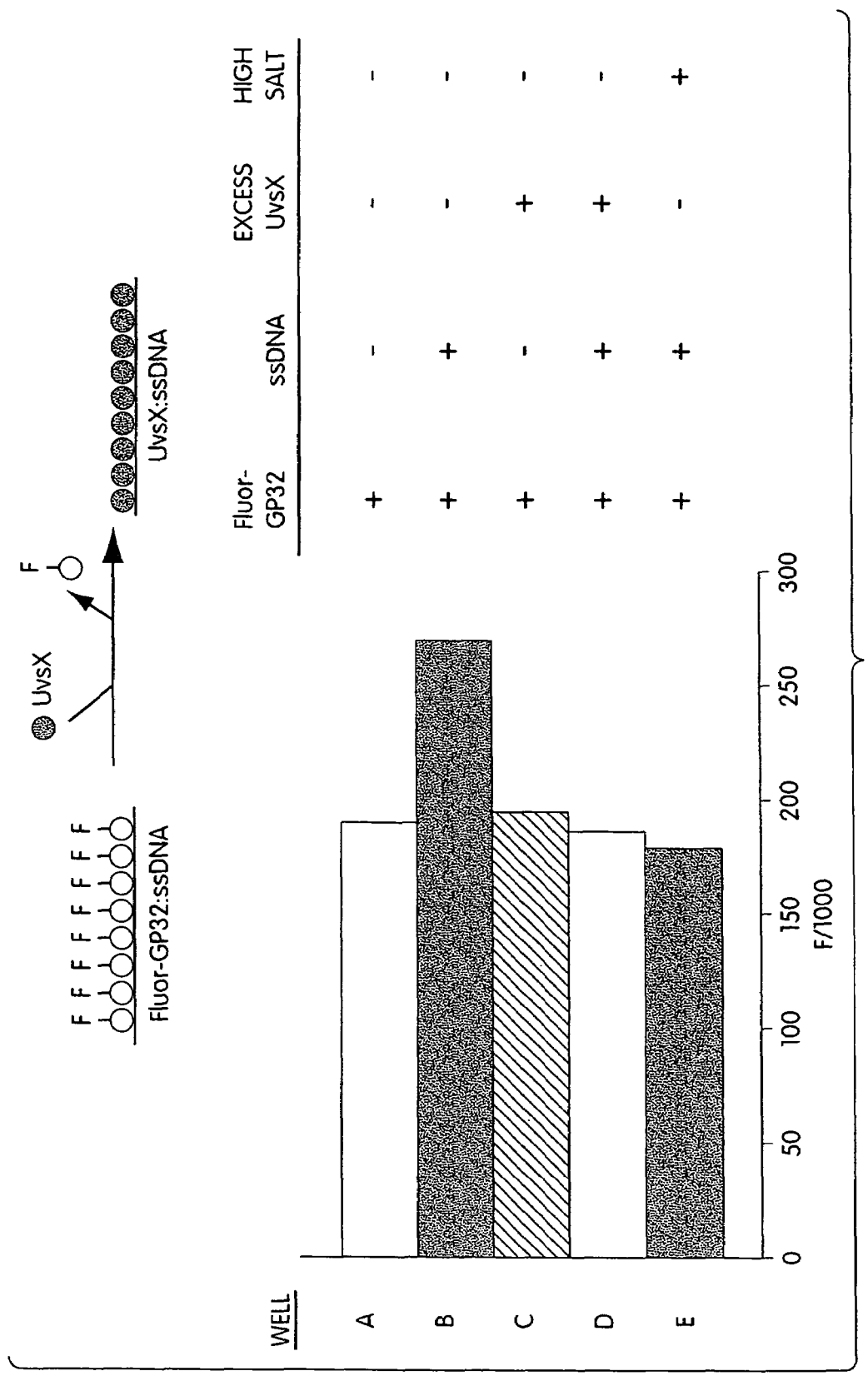
FIG. 8 shows a schematic illustration of a "Taqman" fluorescence plate reader assay for protein-ssDNA interactions.

The total volume of each well was 100 µl with the buffer containing 20 mM Tris-HCl, pH 7.3, 2 mM $MgCl_2$ and 50 mM NaCl. The plate was read at room temperature (~22 degrees C.) with the excitation wavelength=488 nm and emission wavelength from 510-540 nm via External Laser Molecular IMAGER. FIG. 8 shows the results of the experiment, with the wells corresponding to the results as listed (Wells A-E).

B. Spectrum of Gp32F with and without ssDNA

The spectrum was monitored by FELIX-PTI fluorimeter at room temperature (~22 degrees C.). Samples A, B, and C were excited at 300 nm and the spectrum was collected from 480 nm to 580 nm. The highest emission was achieved at 518 nm.

In sample A, the blank buffer contained 20 mM Tris-HCl, pH 7.3, 2 mM $MgCl_2$ and 50 mM NaCl. This signal was subtracted from all data Sample B, which was the blank buffer contained 0.5 µM Gp32F. Sample C was the blank buffer containing 0.5 µM Gp32F and 4 µM M13mp18 ssDNA. (see FIG. 1).

C. Titration Experiments

The titration experiments were monitored by FELIX-PTI fluorimeter at room temperature (~22 degrees C.) under the excitation wavelength of 300 nM. For each titration point the emission at 518 nm was collected.

a). The Salt-Back of Gp32F/ ssDNA Complex.

0.5 µM Gp32F/4 µM M13 mp18 ssDNA complex in the starting buffer 20 mM Tris-HCl, pH 7.3 and 2 mM $MgCl_2$ was titrated by 50 mM NaCl increments until the final concentration of NaCl reached 700 mM.

Figure 7A:
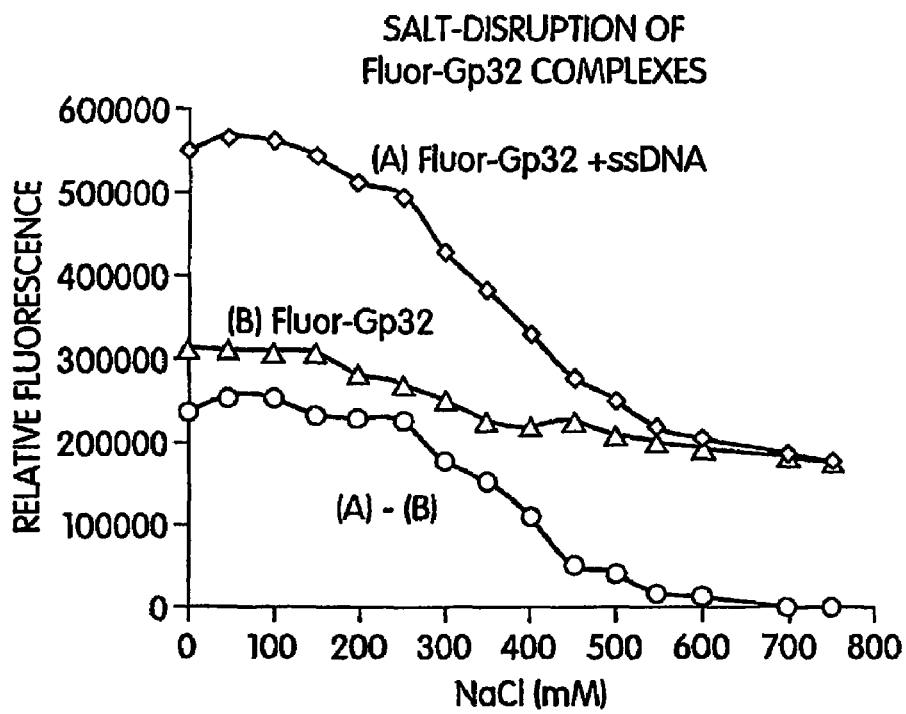
FIG. 7A shows results of salt-disruption of Fluor-Gp32 complexes and FIG. 7B shows displacement by unlabeled Gp32.

0.5 µM Gp32F in the same buffer was titrated with NaCl to make a control curve which was subtracted from the Gp32F/ ssDNA complex salt-back curve. FIG. 7A demonstrates the disruption of Fluorescein-Gp32:ssDNA complex by salt, monitored by loss of fluorescein signal enhancement.

b). The Titration of Gp32F/ ssDNA Complex with Unlabeled Gp32 Protein.

0.5 µM Gp32F /4 µM M13 mp18 ssDNA complex in the buffer 20 mM Tris-HCl, pH 7.3, 2 mM $MgCl_2$ and 50 mM NaCl was titrated by 0.5 µM increments of unlabeled Gp32 until the final concentration of unlabeled Gp32 reached 4 µM.

Figure 7B:
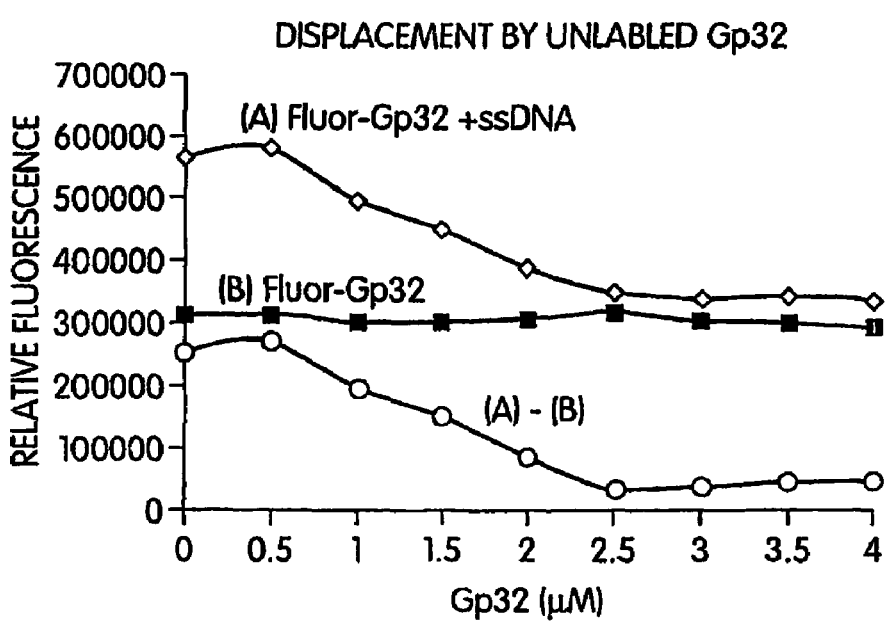

0.5 µM Gp32F in the same buffer was titrated by unlabeled Gp32 to make a control curve which was subtracted from the complex titration curve. FIG. 7B demonstrates the displacement of fluorescein-labeled Gp32 from ssDNA by unlabeled Gp32, monitored by loss of fluorescein signal enhancement.

Example 4

Quantitative Spectrofluorometric Measurements of DNA and RNA Transactions.

The fluorescence properties of Gp32F are used to monitor DNA and RNA reactions that involve conversions between single- and double-stranded states. The polynucleotides are contacted with the Gp32F and the fluorescence of the Gp32F is monitored as a measure of the amount of single-stranded polynucleotide in the reaction. This method is used to monitor reactions such as exonucleolytic degradation of DNA or RNA (FIG. 4A); helicase-catalyzed unwinding of double-stranded DNA, RNA, or RNA-DNA hybrids (FIG. 4B), reannealing of complementary single-stranded polynucleotides to form duplex (FIG. 4C); DNA replication and reverse transcription reactions including replication of primed single-stranded templates and strand displacement DNA synthesis reactions (FIG. 4D); formation of excision gaps during DNA mismatch repair and nucleotide excision repair reactions (FIG. 4E); homologous genetic recombination—DNA strand exchange reactions and presynaptic filament formation (FIG. 4F).

In each reaction, the intensity of the fluorescein probe attached to GP32 at cystein-166 is enhanced upon Gp32F binding to polynucleotide. This allows the assays to be conducted at Gp32F/polynucleotide concentrations at or below the nanomolar threshold given a spectrofluorometer of sufficient sensitivity.

Example 5

Single-molecule Enzymology.

A) Gp32F is added to single-molecule reactions to detect single-stranded polynucleotides in the reactions. The reactions assayed include reactions in which individual DNA or RNA molecules are tethered and single-stranded regions are either generated or consumed depending on the nature of the reaction. Data collection involves either time-resolved imaging or photon counting.

To detect single-stranded polynucleotides in single-stranded enzymology reactions, the DNA and/or RNA molecules are tethered. The tethering is done using standard methods, for example by biotinylating one or both ends of the polynucleotide, allowing it to be tethered at one or both ends to steptavidin-coated polysterene beads. After tethering, the beads (and thus the ends of the DNA or RNA) can be moved and manipulated with "optical tweezers", e.g. a laser-trap system. This method is used to visualize single DNA molecules via fluorescence detection, to perform physical studies of DNA such as stretching and denaturation, and to examine protein-DNA interactions at the single molecule level. The procedure allows detection of the bound Gp32F directly, allowing us to visualization and/or optical imaging of the production or loss of ssDNA or RNA.

The reactions assayed with this method include, but are not limited to exonuclease reactions (see FIG. 4A); helicase reactions (see FIG. 4B); replication and reverse transcription reactions (see FIG. 4D); and recombination—presynaptic filament formation (see FIG. 4F).)

B) A DNA replication fork is observed moving in real-time, by watching Gp32F coat the displaced ssDNA during strand-displacement DNA synthesis. Bacteriophage T4 DNA polymerase holoenzyme (Gp43, Gp44/62, Gp45 proteins) in concert with Gp32 catalyzes strand displacement DNA synthesis beginning at a nick in dsDNA. As DNA polymerization proceeds, the lagging stranded of the template DNA is displaced as ssDNA. The length of the ssDNA grows as the replication fork proceeds along the template. Using "optical tweezers" technology with a tethered DNA template, the growth of the lagging strand ssDNA is monitored by fluorescence imaging of Gp32F progressively binding to the ssDNA as it emerges from the replisome.

Example 6

Quantitative Analysis of Protein-ssDNA and Protein-ssRNA Interactions.

The fluorescence enhancement observed upon Gp32F-polynucleotide binding is used to quantitate other protein-ssDNA or -ssRNA interactions by performing competition experiments in which the displacement of Gp32F from the single-stranded polynucleotide is measured as a function of the second protein's concentration, by following the decrease in Gp32F signal intensity. Binding parameters for the second protein are extracted from competition data of this type as described (Kowalczykowski, S. C., et al. (1986) *Biochemistry*. 25(6), 1226-40.).

Similar competition assays coupling changes in polynucleotide electrophoretic mobility with loss of Gp32F from the complex are used to extract polynucleotide binding parameters of a second protein.

Example 7

Quantification of Single-stranded Polynucleotides.

The solution concentrations of ssDNA and ssRNA molecules are measured by titrating a known concentration of Gp32F with the nucleic acid and determining the endpoint at which no further fluorescence change takes place. Because the binding-site size of Gp32F on single-stranded polynucleotides is known, calculating the precise concentration of ssDNA or RNA in a solution is straightforward by this method. The method provides greatly increased sensitivity compared to absorbance measurements of ssDNA/ssRNA concentration. The method also allows use of the ability of Gp32F to denature secondary structure in single-stranded polynucleotides, which makes this method more accurate than absorbance or fluorescent ssDNA/ssRNA staining procedures, because the latter two signal types are dependent on the degree of secondary structure present.

Example 8

Variations of the Gp32F Protein

Conjugation of different fluorescent probes at the cysteine-166 position of gp32 is done to provide a different wavelength range of fluorescence detection, e.g. for use in a double-labeling experiment or to establish a donor-acceptor pair for fluorescence resonance energy transfer (FRET) experiments. Fluorescent probes that are more environment-sensitive than fluorescein are also conjugated at cysteine-166, to yield a larger change in fluorescence upon polynucleotide binding, therefore improving the sensitivities of various assays.

Fluorescent labeling of cysteine-166 in new or existing mutated forms of Gp32 is done to take advantage of changes in polynucleotide binding properties (i.e. enhanced affinity for ssDNA in Gp32-R4K and Gp32-A mutants) and/or protein-protein interactions (Villemain, J. L., et al. (2000) *J Biol Chem*. 275(40), 31496-504.).

Genetic engineering and/or targeted mutagenesis are used to reposition cysteine on the surface of Gp32, allowing labeling with thiol-specific fluorescent probes at different positions. This is done to improve assay sensitivity by enhancing the fluorescence change upon polynucleotide binding, and/or to optimize FRET assays.

Different residues in Gp32 are targeted for fluorescent labeling using non-thiol specific chemistry, and conjugates are identified that have desirable fluorescence properties for use in ssDNA/ssRNA detection.

Fluorescently labeled forms of Gp32 orthologs from related T-even bacteriophages (e.g. bacteriophages T2, T6, RB69, RB49, etc.) are used in the assays provided herein. The resulting protein conjugates with desirable nucleic acid binding and fluorescence properties for use in ssDNA/ssRNA detection are identified.

Improvements in fluorescence microscopy allow simultaneous detection of single- vs. double-stranded regions of nucleic acids via double-labeling (i.e. intercalative dye for duplex, Gp32F or derivative for single-strand). These have utility in heterology mapping of hybridized nucleic acids (DNA/DNA, RNA/DNA, or RNA/RNA), and in single-molecule enzymology.

Gp32F or mutants, variants, and/or derivatives are used as a fluorescence signature for monitoring time-resolved PCR, DNA sequencing, or site-directed mutagenesis reactions.

Example 9

Use Gp32F as Cytological Marker for ssDNA

Gp32F is used to measure efficacy of radiation or chemotherapeutic treatments of tumor cells by identifying and quantifying strand breaks or sites of arrested DNA replication. These sites are typically associated with the accumulation of single-stranded DNA as a result of processing by DNA repair enzymes. Slides prepared from biopsy samples are stained with Gp32F and examined under a fluorescence microscope. Alternatively Gp32F is introduced by microinjection, electroporation or other methods into whole cells retrieved via biopsy and sites of Gp32F localization observed via confocal fluorescence microscopy.

Example 10

Real-time Classic Enzymology in Bulk Solution:

Measure the reannealing of complementary DNA strands, providing information on the sequence complexity and thermal stability of double-stranded DNA molecules. Result is monitored via fluorescence signal decrease caused by Gp32F dissociation as ssDNA→dsDNA. This application is used to optimize the design of PCR primers and other applications requiring DNA/DNA, RNA/DNA, or RNA/RNA reannealing and thermal, chemical or physical manipulation thereof.

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

We claim:

1. A Gp32F protein comprising a Gp32 protein conjugated at an environment-sensitive amino acid to a fluorescent label that fluoresces at a first intensity when the Gp32 protein is not bound to a single-stranded polynucleotide and fluoresces at a second intensity when the Gp32 protein is bound to a single-stranded polynucleotide.

2. The Gp32F protein of claim 1, wherein the environment-sensitive amino acid is selected from the group consisting of cysteine-166, Serine-195 mutated to cysteine, Lysine-51 and Lysine-207.

3. The Gp32F protein of claim 1, wherein the Gp32 protein is a mutant Gp32 protein.

4. The Gp32F protein of claim 3, wherein the mutant Gp32 protein is a truncated Gp32 protein.

5. The Gp32F protein of claim 1, wherein the fluorescent label is selected from the group consisting of fluorescein, BODIPY, Alexa Fluor, Oregon Green, tetramethylrhodamine, Rhodamine Red, Texas Red, pyridyloxazole,; benzoxadiazole derivatives including NBD halides and iodoacetamides, SBD; Lucifer Yellow, iodoacetamide; stilbene, coumarin, napthalene, aziridine, dapoxyl, pyrene, and bimanes.

6. The Gp32F protein of claim 1, wherein the single-stranded polynucleotide is tethered to a surface.

7. A method of detecting single-stranded polynucleotides in a sample, comprising:
   (a) contacting a sample with a Gp32F protein of claim 1, and
   (b) detecting fluorescence of the Gp32F protein bound to the sample as an indication of single-strand polynucleotides in the sample, and optionally, the method further comprising a step of separating bound Gp32F protein from unbound Gp32F protein.

8. The method of claim 7, wherein the sample comprises a tissue, cell, or fragment thereof.

9. The method of claim 8, further comprising determining the localization of the single-stranded polynucleotides in the cell, tissue, or fragment thereof.

10. The method of claim 7, wherein the single-stranded polynucleotide is a gap, tail, flap, loop, or bubble in a double-stranded polynucleotide.

11. A method of determining the quantity of single-stranded polynucleotide in a sample, comprising,
   (a) contacting a sample with a Gp32F protein of claim 1, and
   (b) determining the intensity of fluorescence in the sample, wherein the intensity of fluorescence indicates the quantity of single-stranded polynucleotide in the sample, the method optionally further comprising a step of separating Gp32F protein bound to single-stranded polynucleotides in the sample from unbound Gp32F protein, and/or the method optionally further comprising comparing the intensity detected in step (b) with a control intensity as an indication of the quantity of single-stranded polynucleotide in the sample.

12. The method of claim 11, wherein the control intensity is the level of fluorescence in the Gp32F protein not contacted with the sample or is a standard curve of fluorescence intensity.

13. The method of claim 11, wherein the sample comprises a reaction selected from the group consisting of: exonucleolytic degradation of DNA or RNA; helicase-catalyzed unwinding of double-stranded DNA, RNA, or RNA-DNA; reannealing of complementary single-stranded polynucleotides to form duplex; DNA replication; DNA reverse transcription, formation of excision gaps during DNA mismatch repair; nucleotide excision repair reactions; homologous genetic recombination-DNA strand exchange reactions; and presnaptic filament formation.

14. The method of claim 11, wherein the sample comprises a tissue, cell, or fragment thereof.

15. The method of claim 14, further comprising determining the localization of the single-stranded polynucleotides in the cell, tissue, or fragment thereof.

16. The method of claim 11, wherein the single-stranded polynucleotide is a gap, tail, flap, loop, or bubble in a double-stranded polynucleotide.

17. The method of claim 11, wherein the step of determining the level of fluorescence is done in real-time, wherein a change in the level of fluorescence over time indicates a change in the quantity of single-stranded polynucleotide in the sample over time.

* * * * *

SEQUENCE LISTING

```
<160> NUMBER OF SEQ ID NOS: 1

<210> SEQ ID NO 1
<211> LENGTH: 301
<212> TYPE: PRT
<213> ORGANISM: Enterobacteria Phage T4

<400> SEQUENCE: 1

Met Phe Lys Arg Lys Ser Thr Ala Glu Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Asn Ala Gly Asn Gly Gln Ala Val Ile Arg Phe Leu
        35                  40                  45

Pro Ser Lys Asn Asp Glu Gln Ala Pro Phe Ala Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asp Asn Lys Glu Tyr Ser Leu Val Lys Arg Lys
            100                 105                 110

Thr Ser Tyr Trp Ala Asn Ile Leu Val Val Lys Asp Pro Ala Ala Pro
        115                 120                 125

Glu Asn Glu Gly Lys Val Phe Lys Tyr Arg Phe Gly Lys Lys Ile Trp
    130                 135                 140

Asp Lys Ile Asn Ala Met Ile Ala Val Asp Val Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
        195                 200                 205
```

-continued

```
Leu Phe Glu Gln Met Val Asp Leu Ser Glu Met Thr Ser Lys Asp Lys
        210             215             220

Phe Lys Ser Phe Glu Glu Leu Asn Thr Lys Phe Gly Gln Val Met Gly
225             230             235             240

Thr Ala Val Met Gly Gly Ala Ala Ala Thr Ala Ala Lys Lys Ala Asp
            245             250             255

Lys Val Ala Asp Asp Leu Asp Ala Phe Asn Val Asp Asp Phe Asn Thr
        260             265             270

Lys Thr Glu Asp Asp Phe Met Ser Ser Ser Ser Gly Ser Ser Ser Ser
        275             280             285

Ala Asp Asp Thr Asp Leu Asp Asp Leu Leu Asn Asp Leu
    290             295             300
```